United States Patent [19]

Hohmann

[11] Patent Number: 4,479,823
[45] Date of Patent: Oct. 30, 1984

[54] PROCESS FOR THE PRODUCTION OF SILVER-TIN MASTER ALLOYS FOR DENTAL AMALGAMS

[75] Inventor: Wolfgang Hohmann, Frankfurt am Main, Fed. Rep. of Germany

[73] Assignee: Blendax-Werke R. Schneider GmbH & Co., Mainz, Fed. Rep. of Germany

[21] Appl. No.: 545,208

[22] Filed: Oct. 25, 1983

[30] Foreign Application Priority Data

Oct. 30, 1982 [DE] Fed. Rep. of Germany ....... 3240256

[51] Int. Cl.$^3$ ................................................ B22F 9/00
[52] U.S. Cl. .................................. 75/0.5 R; 75/0.5 C; 264/6; 264/11; 264/12
[58] Field of Search ............... 75/0.5 R, 0.5 B; 264/6, 264/11, 12

[56] References Cited

U.S. PATENT DOCUMENTS

| 2,271,264 | 1/1942 | Kaufmann et al. | 420/501 |
|---|---|---|---|
| 3,305,356 | 2/1967 | Youdelis | 75/0.5 B |
| 3,871,876 | 3/1975 | Asgar et al. | 75/251 |
| 3,954,457 | 5/1976 | Welkel | 420/502 |
| 3,975,192 | 8/1976 | Simpson | 420/502 |
| 3,980,472 | 9/1976 | Asgar et al. | 420/502 |
| 3,997,329 | 12/1976 | Aliotta et al. | 420/502 |

Primary Examiner—W. Stallard
Attorney, Agent, or Firm—Connolly and Hutz

[57] ABSTRACT

A silver-tin-copper master alloy powder useful as a dental filling when amalgamated with mercury and having improved properties for that utility can be obtained by the steps of:

(a) pulverizing an alloy containing silver, tin and copper into a first spherical powder by high pressure water, inert gas or similar pulverization
(b) drying and forming said first powder into a coherent shaped article;
(c) sintering the shaped article at an elevated temperature; and
(d) pulverizing the sintered shaped article by machining into a master alloy powder.

12 Claims, No Drawings

PROCESS FOR THE PRODUCTION OF SILVER-TIN MASTER ALLOYS FOR DENTAL AMALGAMS

BACKGROUND

The invention relates to a process for the production of silver-tin master alloys for dental amalgams having improved stability and processibility.

As known, amalgams are extensively used as filling materials in dental care.

The preparation of the amalgam in dental practice takes place immediately before the filling is to be applied by mixing mercury with silver-containing master alloys.

These master alloys as a rule comprise the main components silver and tin to which minor pecentages of other metals, in particular, copper are added.

The composition of these alloys predominantly correspond to the formula $Ag_3Sn$. This composition is very brittle and produces fine crumbling chips when machined by milling or turning which chips can be optionally further reduced in size by subsequent grinding.

It is assumed that during amalgamation, part of this $Ag_3Sn$ ($\gamma$-phase) is converted to a silver-mercury compound ($\gamma_1$-phase) and a tin-mercury compound ($\gamma_2$-phase). The latter corresponds approximately to the composition $Sn_8Hg$ and is responsible for the corrosion sensitivity of this type amalgam which results from its high tin content.

The corrosion sensitivity can be substantially reduced by alloying the silver-tin master alloy with about 10 to about 25% copper. In this silver-tin-copper master alloy copper-tin compounds such as $Cu_6Sn_5$ or $Cu_3Sn$ are formed instead of $Sn_8Hg$ as a result of higher affinity of copper to tin. The amalgams produced from such master alloys are therefore then extensively free from the $\gamma_2$-phase and substantially more corrosion resistant than the conventional silver-tin amalgams with acceptable silver content.

However, alloying with copper has certain drawbacks and disadvantages in the producibility of the pulverized master alloys and the advantage of the copper addition becomes questionable.

In order to obtain a good tamping of the alloy, a high edge strength of the filling and a certain tolerance in mercury dosage, pulverized alloys produced by machining are used predominantly. However, silver-tin-copper alloys can only be machined within a range of content of about 40% slver, 30% tin and 25 to 30% copper with the alloy having a ratio of about 3:2 of the brittle intermetallic compounds $Ag_8Sn$ and $Cu_3Sn$. Amalgams produced from this alloy have as a result, a high copper content, they harden very slowly compared to the conventional amalgams and do not show the true silvery brilliance with the suggested zinc addition.

The currently commercially available products mostly comprise machined silver-tin alloys having a content of about 70% silver and 30% tin admixed with a pulverized silver-copper eutectic. Since this spherical pulverized powder must be finer than the chips, the yield from the pulverizing process is only about 25%. This pulverized powder is per se extremely corrosion sensitive and the powder mixtures produced in this way can only be stored under vacuum or absolute air exclusion and tend to separate during transport and processing. The amalgms produced from these powders are, moreover, uneconomical since their silver content is much higher than necessary.

With respect to desired composition, optimum master alloys for the preparation of amalgams are master alloys containing about 40 to 70% (preferably 50 to 60%) of silver, about 10 to 25% (preferably 12 to 15%) of copper and up to a maximum of 30% (preferably 20 to 30%) of tin and optionally other metals in minor amounts (for example, up to a maximum of 2% zinc). These alloys form long chips, however, as a result of their tenacity. Powders of these compositions can only be produced by pulverization with high pressure water or inert gas but powders pulverized in that way in general have the additional disadvantage that they can be poorly tamped. Their use requires a very precise mercury dosage and presupposes a very fine particle size. Also, the edge strength is poorer than in fillings produced from machined alloys.

BRIEF DESCRIPTION OF THE INVENTION

According to the invention it has been found that, for the preparation of dental amalgams, preferred suitable master alloys having optimum properties can be produced from chip-shaped powder when the alloys are first pulverized by high pressure water or inert gas methods and the thus obtained powder is then processed into a shaped porous, sintered article and chip-shaped secondary powders are obtained by machining the article.

DETAILED DESCRIPTION OF THE INVENTION

The tenacious chip-shaped master alloys obtained by the method of this invention has a high mechanical strength and superior corrosion resistance. This leads to a high edge strength and an equal dimensional stability without simultaneous brittleness. Also, the powders can be easily tamped, have a sufficient dosage tolerance with respect to the mercury components, harden quickly during amalgamation, have a high storage stability, do not separate and are, moreover, generally economical since the silver content can be kept relatively low.

The production process of the invention is conducted as follows:

The alloys preferably having the above cited desired composition are first pulverized into spherical powders. All known pulverization methods to produce spherical powders can be used. For example, the mostly used method of inert gas pulverization and, also, the high pressure water method are preferred for the pulverization of the alloys. This first step pulverization produces particles in a size range greater than conventional.

The powders thus obtained are dried and formed in a known manner to square blocks or round rods. The square blocks are preferably pressed mechanically, for example, in the molding process, and the rods preferably isostatically.

The pressed articles are then subjected to a sintering in the recrystallization temperature range of about 150°–350° C. for about half an hour under reducing atmosphere. Examples of suitable reducing atmospheres are hydrogen under 100-1050 mbar. Thus obtained sintered articles are then pulverized by machining into a master alloy powder suitable for amalgamation with mercury to produce a dental filling. The strength of the porous sintered articles obtained is sufficient to conduct pulverization by machining, for example, by milling or turning, and pulverization by conventional means.

As a result of the high porosity of the sintered articles, short crumbling particle chips are produced even with alloys which produce basically long chip particles when conventionally processed. As a result of chip deformation, the average particle sizes produced by this invention are clearly below the average particle sizes of the starting powder.

The chipped master alloys produced in this way are interspersed with the finest, partly adhering, spherical particles which results in an additional quality improvement.

The invention is further illustrated by, but is not intended to be limited to the following detailed examples.

EXAMPLES

1. A powder produced by inert gas pulverization of the composition 56% Ag, 15% Cu, and 29% Sn with a particle size range of 100–160 $\mu$um is isostatically pressed by 8 kbar, sintered for 30 minutes at 300° C. under 100 mbar hydrogen atmosphere, machined by turning, recrystallized for 30 minutes at 280° C. under 100 mbar hydrogen atmosphere, milled, and sieved through a suitable mesh sieve to give an alloy with excellent mechanical properties when filled into dental cavities after amalgamation.

2. A powder prepared by high pressure water pulverization having the composition 54% Ag, 18% Cu, and 28% Sn, with a particle size range of 160–250 $\mu$um was isostatically pressed by 8 kbar, sintered for 60 minutes at 250° C. under 100 mbar hydrogen atmosphere, machined by turning, recrystallized for 20 minutes at 300° C. under 100 mbar hydrogen atmosphere, milled, and sieved through a suitable mesh sieve.

An alloy was obtained giving properties similar to the alloy of Example 1 when amalgamated and brought into a dental cavity.

What is claimed is:

1. A process for the production of a master alloy powder with improved properties for producing dental filling material when amalgamated with mercury, comprising the steps of:
   (a) atomizing an alloy containing silver, tin and copper into a first spherical powder;
   (b) drying and forming said first powder into a coherent shaped article;
   (c) sintering the shaped article at an elevated temperature; and
   (d) pulverizing the sintered shaped article into a master alloy powder.

2. The process according to claim 1 wherein said first powder as in step (b) formed into a coherent shaped article having the shape of a square block or a round rod.

3. The process according to claim 1 wherein the sintering of step (c) is conducted in a reducing atmosphere.

4. The process according to claim 1 wherein the sintering of step (c) is conducted at a temperature range of 150 to 350° C.

5. The process according to claim 1 wherein atomization is by the high pressure water process.

6. The process according to claim 1 wherein the master alloy powder obtained in step (d) has a lower average particle size than the first powder obtained in step (a).

7. The process according to claim 1 wherein pulverization is accomplished by machining.

8. The process according to claim 7 wherein the machining involves milling.

9. The process according to claim 7 wherein the machining involves turning.

10. The process according to claim 1 wherein said first powder is shaped into a coherent article by mechanical pressing.

11. The process according to claim 1 wherein said first powder is shaped into a coherent article isostatically in the form of a rod.

12. The process according to claim 1 wherein pulverization is by inert gas atomization.

* * * * *